United States Patent [19]
Raybone et al.

[11] Patent Number: 6,012,326
[45] Date of Patent: *Jan. 11, 2000

[54] DETECTION OF VOLATILE SUBSTANCES

[75] Inventors: David Raybone, Gloucester; Fiona Winterbottom, Oxford; Robert Frew Gillespie, Abingdon; Stephen Ivor Hall, Oxford, all of United Kingdom

[73] Assignee: AEA Technology plc, Didcot, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/901,206

[22] Filed: Jul. 28, 1997

[30] Foreign Application Priority Data

Aug. 10, 1996 [GB] United Kingdom .................. 9616841

[51] Int. Cl.[7] .................. H05H 1/30; H05H 1/34
[52] U.S. Cl. .................. 73/31.02; 73/31.03; 422/186.21; 422/186.22; 422/906
[58] Field of Search .................. 73/31.01, 31.02, 73/31.03, 24.01, 24.02; 422/186.21, 186.22, 906

[56] References Cited

U.S. PATENT DOCUMENTS

| | | | |
|---|---|---|---|
| 3,843,257 | 10/1974 | Wooten | 356/85 |
| 4,532,219 | 7/1985 | Hagen et al. | 436/155 |
| 4,615,225 | 10/1986 | Sainz | 73/864.33 |
| 5,340,450 | 8/1994 | Griffiths et al. | 204/157.3 |
| 5,503,807 | 4/1996 | Griffiths et al. | 422/186.04 |
| 5,596,405 | 1/1997 | Seltzer | 356/316 |

FOREIGN PATENT DOCUMENTS

| | | |
|---|---|---|
| 4-168350 | 6/1992 | Japan . |
| 2273027 | 6/1994 | United Kingdom . |
| WO 95/11442 | 4/1995 | WIPO . |

*Primary Examiner*—Daniel S. Larkin
*Attorney, Agent, or Firm*—William H. Holt

[57] ABSTRACT

An apparatus for detecting the presence of volatile substances in a gaseous medium, including apparatus for producing within a sensor chamber a localised electric field the energy density of which is sufficient to excite the gaseous medium to a plasma condition, and apparatus for detecting changes in a parameter of the plasma due to the presence of the volatile substances in the gaseous medium.

20 Claims, 3 Drawing Sheets

DETECTION OF VOLATILE SUBSTANCES

The present invention relates to the detection of the presence of volatile substances in gaseous media, and more specifically, to the detection of volatile organic compounds in air, or effluent streams.

BACKGROUND OF THE INVENTION

Many volatile organic compounds are toxic or carcinogenic and it is highly desirable that they should be detected readily so that remedial action can be taken, such as changing filters designed to remove such compounds from breathing apparatus or effluent ducts from process plant, or changing the operating parameters of processes which involve the volatile organic compounds or produce them as by-products.

Traditional methods of detecting volatile organic compounds in gaseous media are based on infrared absorption spectroscopy or gas chromatography. Such methods tend to be slow and require cumbersome equipment. Whereas this may be acceptable in the context of process control in a fixed chemical plant, it may not be so for use in the field.

In U.S. Pat. No. 3,843,257 there is disclosed an apparatus and method for detecting materials in gaseous media in which a gaseous medium is irradiated with microwave energy and optical emissions from the excited gaseous medium are analysed to detect the presence of the materials in the gaseous medium.

However, the apparatus and method described includes a preliminary stage in which a particulate or liquid component of a first gaseous medium is atomised and mixed with a carrier gas prior to being subjected to irradiation with microwaves such as to produce an electrical discharge in the carrier gas which causes the emission of optical radiation from the atomised components of the first gaseous medium.

The apparatus therefore is relatively complicated and more suited to laboratory rather than field use.

SUMMARY OF THE INVENTION

It is an object of the present invention to provide apparatus for the detection of volatile substances in gaseous media, which is portable, rugged, and simple to use.

According to the invention in one aspect there is provided an apparatus for detecting the presence of a volatile substance in a gaseous medium, the apparatus comprising a chamber, means for enabling a gaseous medium, the presence in which a volatile substance is to be detected, to be passed through the chamber, means for producing within the chamber a localized region of electromagnetic field having an energy density which is sufficient to excite the gaseous medium to form a plasma, means for directing said gaseous medium through said region of electromagnetic field, and means for detecting changes in a parameter of the plasma due to the presence of a volatile substance in the gaseous medium.

The changes in the state of the plasma due to the presence of the volatile substances may be changes in the temperature of the plasma due to reactions between the gaseous medium and the volatile substance occurring in the plasma; the efficiency of absorption of the radiation by the gaseous medium, or optical emissions from excited states of the volatile substance or reaction products derived from it.

A particular form of volatile substance for the detection of which in a gaseous medium the present invention is suitable, is volatile organic compounds, and a particularly suitable form of radiation is microwave radiation, although other forms of radiation such as laser radiation can be used.

According to the present invention, there is provided a method of detecting the presence of a volatile substance in a gaseous medium, comprising the steps of producing within a gaseous medium, comprising the steps of producing within a localized region of a chamber an electromagnetic field having an energy density sufficient to produce a plasma within the gaseous medium, directing the gaseous medium through the region of the chamber, and detecting changes in a parameter of the plasma due to the presence of a volatile substance within said gaseous medium.

Preferably, the means for detecting changes in the state of the plasma due to the presence of the volatile substance comprises means for detecting specific optical emissions from excited species arising from the volatile substances in the plasma.

The means for detecting specific optical emissions from excited species arising from the volatile substances in the plasma may comprise at least one photosensitive device associated with an optical filter adapted to select the specific optical emissions arising from the volatile substance in the plasma.

Alternatively, the means for detecting changes in the condition of the plasma due to the presence of the volatile substance in the plasma may comprise means for measuring the temperature of the plasma.

Another means for detecting changes in the condition of the plasma due to the presence of the volatile substance in the plasma may comprise means for measuring changes in the efficiency of the coupling of the exciting radiation into the plasma.

Preferably, the means for exciting the gaseous medium to the plasma state comprises means for coupling microwave radiation into the chamber and there is included within the chamber a pair of electrodes adapted to produce a region of enhanced electric field in the vicinity of the electrodes so as to produce the localised plasma in the gaseous medium in the chamber.

BRIEF DESCRIPTION OF THE DRAWINGS

The invention will now be described, by way of example, with reference to the accompanying drawings, in which.

Referring to FIG. 1 of the drawings, a sensor for detecting the presence of volatile organic compounds in a gaseous medium consists of a chamber 101 comprised of two stainless steel end-plates 102 and 103, a cylindrical wall 104 made of a material which is transparent to the radiation which it is anticipated will be emitted by substances for the detection of which the sensor will be used, the wall 104 being mounted in the end-plates 102 and 103 and rendered gas tight by means of O-ring seals 105. An appropriate material, for wall 104, for use when the emitted radiation lies in the optical and ultra-violet regions of the spectrum is quartz. An outer wall 106 forms part of a waveguide by means of which energy is supplied to the chamber 101. The assembly is clamped together by set screws, which are not shown in the drawing. Also included, but not shown in the drawing is means for coupling microwave radiation into the interior of the chamber 101. Mounted in the outer wall 106 are a number of optical ports 107, two of which are shown in the drawing. Each optical port 107 has a lens 108 which focuses light emitted within the chamber 101 into an associated optical fibre 109. Each of the end-plates 102 and 103 has a conical protuberance 110 and 111, respectively, which terminate in a sharp annular tip 112 and 113, respectively. The tips 112 and 113 are screwed into their respective end plates 102 and 103 so that they can be replaced as and when necessary. Suitable materials for the tips 112 and 113 is molybdenum or tungsten, or a similar refractory metal. The conical protuberances 110 and 111 form a pair of electric field enhancing electrodes. The optical ports 107 are so positioned as to observe the gap 120 between the field enhancing electrodes 110 and 111.

Figure 1:
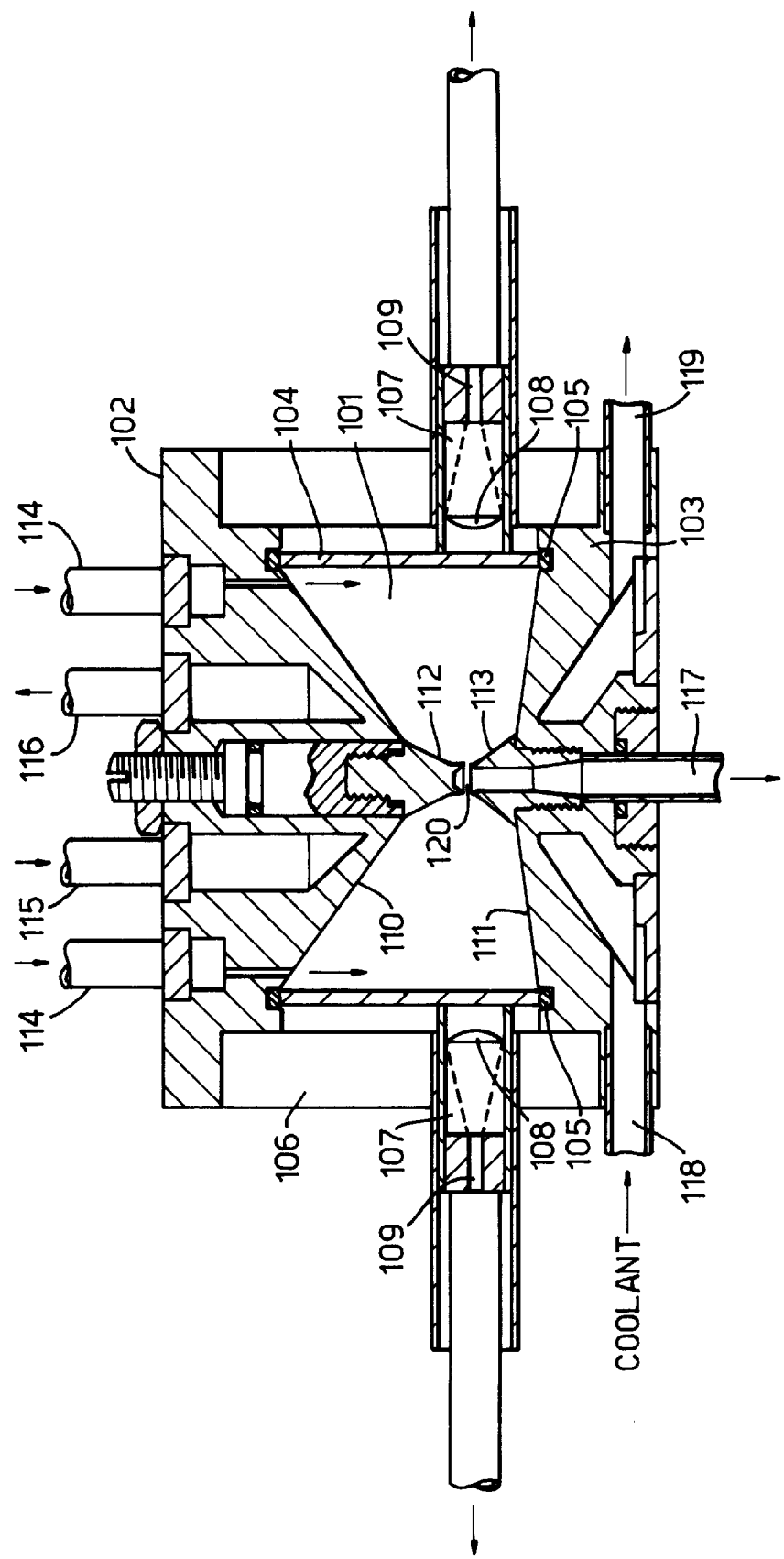
FIG. 1 is a section of a sensor for use in carrying out the present invention.

The end plate 102 has two entry ports 114 for the gaseous medium, the presence in which volatile organic compounds are to be detected, and an inlet 115 and an outlet 116 for a coolant medium. The tip 113 and the end plate 103 have an axial hole 117 by means of which the gaseous medium is extracted from the chamber 1. Again, the end plate 103 is hollow and there is an inlet 118 and an outlet 119 for a cooling medium. The gap 120 between the tips 112 and 113 of the protuberances 110 and 111 on the end plates 102 and 103 is adjustable between 0.1 and about 5 mm. The assembly provides a pair of electrodes 110 and 111 which are spaced for defining the gap 120.

Figure 2:
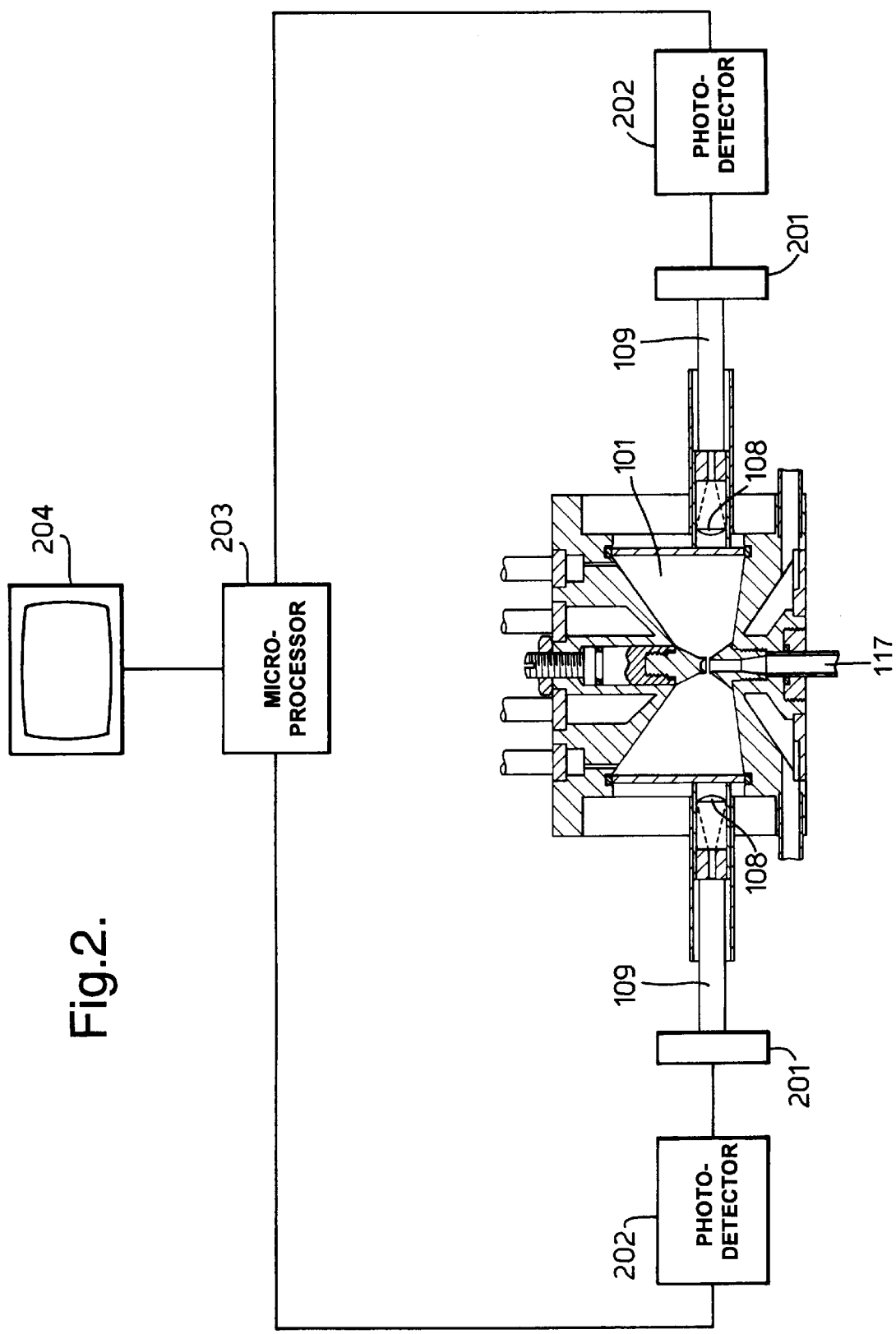
FIG. 2 is a block diagram of an apparatus including the sensor of FIG. 1 for carrying out the present invention.

Referring to FIG. 2, in use, the gaseous medium is passed through the chamber 101 at a pressure in the range 0.001 to 1 bar, and microwave radiation at a frequency of 2.45 Ghz and power of up to 500 watts is coupled into the chamber 101 in such a manner that the electrodes provided by the protuberances 110 and 111 of the end-plates 102 and 103, respectively of the chamber 101, are transverse to the direction of propagation of the microwaves through the chamber 101. The electrodes 110 and 111 concentrate the microwave radiation in the chamber 101 to such an extent that the gaseous medium is excited to the plasma state in the region of the gap 120 between them.

Referring to FIG. 2 of the drawings, optical radiation emitted by the plasma in the chamber 101 is collected by the lenses 108 and focused into the optical fibers 109 and then transmitted via optical filters 201 to photodetectors 202. The output signals from the photodetectors 202 are applied to a microprocessor 203 and an indication of the presence of any volatile organic compounds in the gaseous medium is displayed on a visual display unit 204.

The optical filters 201 are arranged to select spectral regions in which emission bands arising from excited species of interest are expected to occur and the photodetectors 202 provide integrated light intensity emissions in those ranges. For example, if the gaseous medium includes a nitrogenous carrier gas, such as air or nitrogen then, if volatile organic compounds also are present, the expected excited species include CN, CH, or $C_2$ radicals.

Specifically, for example, toluene can be detected in an air stream by using a narrow band width optical filter, centered at 387 nm. Such an optical filter selects emission on the $\Delta v=0$ vibrational sequence of the B→x electronic transition of the CN radical.

Alternatively, if the gaseous medium is oxidising (air or oxygen), the optical filters 201 may be such as to isolate emission bands from excited oxidation products of the volatile organic compounds.

Gases which would not themselves produce detectable radiation can be detected by reacting them with a second gas, to form products which can produce detectable radiation as a result of plasma energisation. For example, if it is desired to detect carbon tetrafluoride in the exhaust from a semiconductor wafer processing plant, then normally no detectable radiation would be produced. However, if the carbon tetrafluoride is mixed with nitrogen then the radical CN would be produced which, as above, does produce detectable radiation.

In another variant of the method, a gaseous medium in which non-radiation producing compounds are to be detected is passed through a plasma generator such as that disclosed in our patent GB 2 273 027 and there converted to species which are capable of being excited to produce optical radiation. These precursor species are then passed through the sensor of the present invention, excited to a plasma state, and the optical radiation analysed as before.

It is not necessary for the volatile organic compound to be decomposed in the plasma, emission bands from rotationally or vibrationally excited molecules of the volatile organic compound can be detected.

Figure 3:
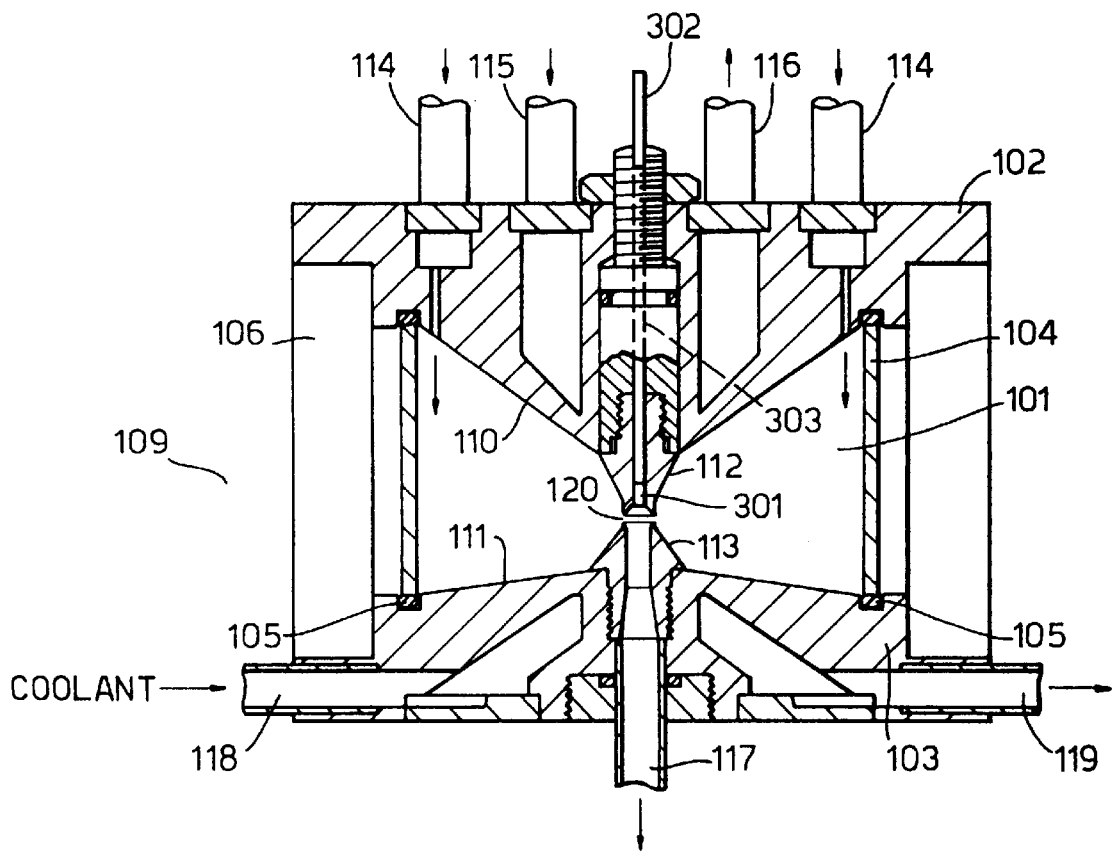
FIG. 3 shows an alternative optical radiation detector for use in a sensor embodying the present invention.

Referring to FIG. 3 there is shown a second form of sensor for use in carrying out the present invention.

In the sensor shown in FIG. 3, the optical parts 107, lenses 108, and optical fibers 109 are omitted and are replaced by a single photodiode 301 and associated optical fibre 302 which are mounted axially in a bore 303 in the electrode 110. The remainder of the sensor is the same as that described with reference to FIG. 1 and the same reference numerals are used.

Figure 4:
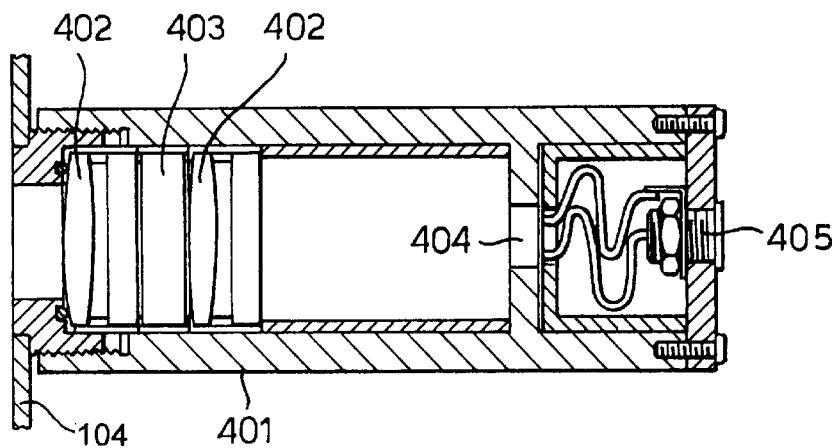
FIG. 4 shows another optical radiation detector for use in a sensor embodying the invention.

Referring to FIG. 4, there is shown an alternative form of optical port 107, which consists of a housing 401 which is adapted to be mounted in the cylindrical wall 104 of the sensor so as to observe the gap 120 between the tips 112 and 113 of the electrodes 110 and 111, as before. Inside the housing 401 is a lens system 402 which includes a number of appropriate optical filters 403, a photodiode 404, and an output socket 405.

In other forms of the apparatus, which are not illustrated, the detectors of optical radiation from the plasma are omitted and replaced by means, such as a thermocouple for measuring the temperature of the plasma as this parameter is affected by the heat of formation of reaction products between the gaseous medium and volatile compounds contained in it, or by means for measuring the efficiency of the coupling of the exciting radiation into the chamber 101, as again, this parameter will be affected by the presence in the gaseous medium of the volatile substance, and products derived from it. This may be done by incorporating a power meter in the waveguide feeding the chamber 101.

We claim:

1. An apparatus for detecting the presence of a volatile substance in a gaseous medium, said apparatus comprising a chamber, means for enabling a gaseous medium, the presence in which a volatile substance is to be detected, to be passed through said chamber, means for producing within said chamber a localized region of electromagnetic field having an energy density which is sufficient to excite said gaseous medium to form a plasma, means for directing said gaseous medium through said region of electromagnetic field, and means for detecting changes in a parameter of said plasma due to the presence of a volatile substance in said gaseous medium.

2. An apparatus according to claim 1 wherein the means for detecting changes in a parameter of the plasma due to the presence of the volatile substance in the gaseous medium comprises means for measuring the temperature of the plasma.

3. An apparatus according to claim 1 wherein the means for irradiating a region of the chamber with radiation the energy density of which is sufficient to excite the gaseous medium to the plasma state comprises a laser.

4. Apparatus for detecting the presence of a volatile substance in a gaseous medium, said apparatus comprising a chamber; means for passing through said chamber a gaseous medium, in which the presence of a volatile substance is to be detected; means for producing an electromagnetic field in a localized region of said chamber; said electromagnetic field having an energy density sufficient for exciting said gaseous medium to form a plasma; means for directing said gaseous medium through said localized region; and means for detecting changes in a parameter of said plasma when a volatile substance is present in said gaseous medium.

5. Apparatus as defined in claim 4 including a pair of opposed field enhancing electrodes included in said chamber and having a space therebetween, at least one of said electrodes including a passage which opens into said space and communicates outwardly of said chamber.

6. Apparatus as defined in claim 4 wherein said means for detecting changes comprises means for detecting specific optical emissions from said volatile substance.

7. Apparatus as defined in claim 4 wherein said means for detecting changes comprising means for measuring the temperature of said plasma.

8. Apparatus as defined in claim 7 wherein said means for measuring the temperature of said plasma comprises a thermocouple.

9. Apparatus as defined in claim 4 wherein said means for producing said electromagnetic field comprises a source of microwave radiation, said means for detecting changes comprises means for measuring the efficiency of a coupling of the radiation into said chamber.

10. Apparatus as defined in claim 4 wherein said means for producing said electromagnetic field comprises a laser.

11. A method of detecting the presence of a volatile substance in a gaseous medium, said method comprising the steps of producing within a localized region of a chamber an electromagnetic field having an energy density sufficient to produce a plasma within said gaseous medium, directing said gaseous medium through said region of said chamber, and detecting changes in a parameter of said plasma due to the presence of a volatile substance within said gaseous medium.

12. A method as defined in claim 11 wherein said step of detecting changes includes the step of detecting optical emissions from said volatile substance.

13. A method as defined in claim 11 wherein said step of detecting said changes includes the step of detecting changes in the temperature of said plasma resulting from reactions in said plasma between said gaseous medium and said volatile substance.

14. A method as defined in claim 11 wherein the step of producing said plasma includes the step of exciting said gaseous medium with microwave radiation, and said step of detecting changes includes the step of detecting changes in the efficiency of a coupling of said microwave radiation into said gaseous medium for maintaining said plasma therein.

15. A method as defined in claim 14 including the step of creating radicals from said volatile substance by means of said microwave radiation.

16. A method as defined in claim 14 including the step of creating reaction products from said volatile substance by means of said microwave radiation.

17. A method according to claim 11 including the step of detecting said volatile substance in the form of a volatile organic compound.

18. A method as defined in claim 11 including the step of selecting said gaseous medium to be nitrogenous.

19. A method as defined in claim 18 includes the step of exciting said nitrogenous gaseous medium for creating CH, CN or $C_2$ radicals.

20. A method according to claim 11 including the step of converting said volatile substance from a first form which does not produce detectable optical radiation to a second form which does produce detectable optical radiation when excited to a plasma state.

* * * * *